United States Patent [19]

Tsuchida et al.

[11] Patent Number: 5,272,067
[45] Date of Patent: Dec. 21, 1993

[54] PROCESS FOR PRODUCING L-GLUTAMIC ACID

[75] Inventors: Takayasu Tsuchida; Mitsuyoshi Seki; Haruo Uchibori; Hiroki Kawashima; Hitoshi Enei, all of Kawasaki, Japan

[73] Assignee: Ajinomoto Co., Inc., Tokyo, Japan

[21] Appl. No.: 830,530

[22] Filed: Feb. 4, 1992

Related U.S. Application Data

[63] Continuation of Ser. No. 553,741, Jul. 18, 1990, abandoned.

[30] Foreign Application Priority Data

Jul. 19, 1989 [JP] Japan .................. 1-186282

[51] Int. Cl.$^5$ .................. C12P 13/14; C12N 1/20; C12N 1/00
[52] U.S. Cl. .................. 435/110; 435/252.1; 435/840; 435/843
[58] Field of Search ............ 435/110, 252.1, 840, 435/843

[56] References Cited

U.S. PATENT DOCUMENTS

| | | | |
|---|---|---|---|
| 3,002,889 | 10/1961 | Kinoshita et al. | 435/111 |
| 3,096,252 | 7/1963 | Motozaki et al. | 435/840 |
| 3,660,235 | 5/1972 | Okumura et al. | 435/108 |

OTHER PUBLICATIONS

ATCC Catalog of Bacteria and Bacteriophages, 17th edition, 1989, p. 64.

*Primary Examiner*—Douglas W. Robinson
*Assistant Examiner*—Deborah K. Ware
*Attorney, Agent, or Firm*—Oblon, Spivak, McClelland, Maier & Neustadt

[57] ABSTRACT

A process for the production of L-glutamic acid comprising growing microorganisms belonging to the genera Brevibacterium and Corynebacterium that are resisted to prumycin.

2 Claims, No Drawings

5,272,067

PROCESS FOR PRODUCING L-GLUTAMIC ACID

This application is a continuation of application Ser. No. 07/553,741, filed on Jul. 18, 1990, now abandoned.

BACKGROUND OF THE INVENTION

1. Field of the Invention

L-glutamic acid is an important amino acid useful as a seasoning and for other purposes. This invention provides an improved fermentation process for producing this amino acid.

2. Discussion of the Background

Already known are the fermentation methods for producing L-glutamic acid, which employ a wild strain of Brevibacterium or Corynebacterium, a strain resistant to glutamic acid analogues, a strain resistant to respiratory inhibitors, such as keto-malonic acid and fluoroacetic acid, or a strain resistant to esculetin.

SUMMARY OF THE INVENTION

The object of this invention is to enhance the fermentation yield of L-glutamic acid, thereby reducing its production cost.

The invention provides a process for producing L-glutamic acid which comprises growing a microorganism belonging to the genus Brevibacterium or the genus Corynebacterium, resistant to prumycin and derivatives thereof, and capable of producing L-glutamic acid; and recovering L-glutamic acid formed and accumulated in the culture liquor.

DETAILED DESCRIPTION OF THE PREFERRED EMBODIMENTS

Studies to solve the above-mentioned problem have led us to find that L-glutamic acid can be produced with a higher yield by the use of mutants resistant to prumycin and derivatives thereof, and derived from the already known, L-glutamate-producing microorganisms of Brevibacterium and Corynebacterium. Prumycin is an antibiotic produced by microorganisms belonging to the genus Bacillus.

Listed below are some examples of the strains of Brevibacterium and Corynebacterium resistant to prumycin, and derivatives thereof, used in this invention.

| | |
|---|---|
| Brevibacterium lactofermentum | AJ 12475 (FERM P-10827, FERM BP-2922) |
| Brevibacterium lactofermentum | AJ 12476 (FERM P-10828, FERM BP-2923) |
| Brevibacterium flavum | AJ 12477 (FERM P-10829, FERM BP-2924) |
| Corynebacterium glutamicum | AJ 12478 (FERM P-10830, FERM BP-2925) |

These strains have been derived from Brevibacterium lactofermentum ATCC 13869, Brevibacterium flavum ATCC 14067 and Corynebacterium glutamicum ATCC 13032, respectively, by mutation.

The mutation may be effected by ordinary methods, such as irradiation with ultraviolet rays or radiant rays, or by treatment with a mutagen, for example, treatment with 200 μg/ml nitrosoguanidine at 0° C. for 20 minutes.

Table 1 shows the experimental result on the medical resistance of these strains.

TABLE 1

| prumycin (mg/ml) | Brevibacterium lactofermentum | | | Brevibacterium flavum | | Corynebacterium glutamicum | |
|---|---|---|---|---|---|---|---|
| | ATCC 13869 | AJ 12475 | AJ 12476 | ATCC 14067 | AJ 12477 | ATCC 13032 | AJ 12478 |
| 0 | 100 | 100 | 100 | 100 | 100 | 100 | 100 |
| 2 | 51 | 115 | 110 | 40 | 100 | 53 | 105 |
| 3 | 23 | 110 | 110 | 0 | 98 | 2 | 99 |
| 4 | 8 | 105 | 104 | 0 | 88 | 0 | 90 |
| 5 | 6 | 100 | 90 | 0 | 70 | 0 | 85 |

L-glutamic acid is produced by using these strains as described below. Cultivation is carried out by using a liquid medium containing saccharic materials (such as sugar juice or waste molasses of sugar canes or beets, and starch hydrolyzates) and non-saccharic materials (such as ascetic acid, ethanol and paraffin). Suitable nitrogen sources, include ammonium salts, ammonia water and urea which are compounds used in ordinary L-glutamic acid fermentation, as well as corn steep liquor (CSL) and amino acids obtained by protein degradation. In addition, inorganic salts, such as phosphates and magnesium salts, and trace nutrients such as thiamin and biotin may also be used as required. Furthermore, inhibitory substances against biotin's action such as polyoxysorbitan monopalmitate and penicillin may also be added to the medium when required.

Cultivation should preferably be carried out under aerobic conditions at a temperature of 24° to 37° C. while maintaining the pH within the range from 6 to 9 by the use of an inorganic or organic acid or base, urea, calcium carbonate or ammonia gas. L-glutamic acid accumulated in the fermentation liquor can be recovered by a proper combination of ion-exchange resin treatment and other known techniques.

The growth degree of the strains in Table 1 was examined according to the procedure described below. Each strain was slant cultured in natural medium (containing 1 g/dl peptone, 1 g/dl yeast extract and 0.5 g/dl NaCl; pH 7.0) for 24 hours. A suspension of the grown cells in sterile water was inoculated to a medium containing 0.5 g/dl glucose, 0.15 g/dl urea, 0.15 g/dl ammonium sulfate, 0.3 g/dl $KH_2PO_4$, 0.1 g/dl $K_2HPO_4$, 0.01 g/dl $MgSO_4.7H_2O$, 0.1 mg/dl $CaCl_2.2H_2O$, 10 γ/dl thiamin hydrochloride, 3 γ/dl biotin, 0.44 mg/dl $Na_2B_4O_7.10H_2O$, 4.85 mg/dl $FeCl_2.6H_2O$, 1.95 mg/dl $CuSO_4.5H_2O$, 0.185 mg/dl $(NH_4)_6MO_7O_{24}.4H_2O$, 44 mg/dl $ZnSO_4.7H_2O$, 0.36 mg/dl $MnCl_2.4H_2O$, and prumycin in an amount shown in Table 1 (pH 7.0), and cultivation was continued for 24 hours. The turbidity associated with the growth of bacteria was determined and the degree of growth is expressed in terms of relative percentage in Table 1. The unit "γ" is the weight unit and 1γ is equal to 1/1,000 mg.

EXAMPLE 1

A culture medium containing 10 g/dl glucose, 0.1 g/dl $KH_2PO_4$, 0.1 g/dl $MgSO_4.7H_2O$, 20 γ/dl thiamin hydrochloride, 36 mg/dl concentrate of bean degradation solution, 2.0 g/dl ammonium sulfate, 1 mg/dl FeSO$_4$.7H$_2$O, 1 mg/dl MnSO$_4$.4H$_2$O and 3 γ/l biotin (pH 7.0) was prepared, and 20 ml of the medium thus obtained was placed in each of 500-ml shake flasks and sterilized by heating at 115° C. for 10 minutes. Each of the strains was inoculated to the sterilized medium and grown at 31.5° C. by using a reciprocating shake culture machine. The pH of the culture liquor was maintained within the range from 6.5 to 8.0 by addition of 5 g/dl calcium carbonate, 2.5 g/dl ammonium sulfate was added after 24 hours, fermentation was terminated after 46 hours, and the yield of L-glutamic acid accumulated was measured.

The result obtained is summarized in Table 2.

TABLE 2

|  | Total Yield of L-Glutamic Acid |
| --- | --- |
| *Brevibacterium lactofermentum* |  |
| ATCC 13869 | 48% |
| AJ 12475 | 54% |
| AJ 12476 | 51% |
| *Corynebacterium glutamicum* |  |
| ATCC 13032 | 45% |
| AJ 12478 | 48% |

EXAMPLE 2

A culture medium containing 100 mg/ml beet molasses (as a reducing sugar) and 1 mg/dl KH$_2$PO$_4$ (pH 7.0) was prepared, and 30 ml of the medium thus obtained was placed in each of 500-ml shake flasks and sterilized by heating at 115° C. for ten minutes. Each of the strains was inoculated to the sterilized medium and grown at 31.5° C. by using a reciprocating shake culture machine, and the pH of the culture liquor was maintained within the range from 6.5 to 8.0 by addition of 400 mg/dl aqueous solution of urea. Polyoxysorbitan monopalmitate was added to a concentration of 4 mg/ml 30 hours after inoculation (when the cells were grown to a predetermined level) to terminate fermentation, and the yield of L-glutamic acid accumulated was measured.

The result obtained is summarized in Table 3.

TABLE 3

|  | Total Yield of L-Glutamic Acid |
| --- | --- |
| *Brevibacterium lactofermentum* |  |
| ATCC 13869 | 57% |
| AJ 12475 | 61% |
| AJ 12476 | 62% |
| *Brevibacterium flavum* |  |
| ATCC 14067 | 56% |
| AJ 12477 | 60% |
| *Corynebacterium glutamicum* |  |
| ATCC 13032 | 53% |
| AJ 12478 | 58% |

What is claimed as new and desired to be secured by Letters Patent of the United States is:

1. A process for producing L-glutamic acid comprising:

growing in a culture medium a strain of a microorganism belonging to the species *Brevibacterium lactofermentum*, *Brevibacterium flavum* or *Corynebacterium glutamicum* which (a) has been subjected to an artificial mutation treatment, (b) has been selected on the basis that said strain displays at least 70% relative growth in the presence of prumycin or derivatives thereof at a concentration of 5 mg/ml compared to said strain's growth in the absence of prumycin, and (c) is capable of producing L-glutamic acid;

recovering L-glutamic acid formed and accumulated in the culture liquor.

2. The process of claim 1 where said microorganism is selected from the group consisting of *Brevibacterium lactofermentum* FERM BP-2922, *Brevibacterium lactofermentum* FERM BP-2923, *Brevibacterium flavum* FERM BP-2924 and *Corynebacterium glutamicum* FERM BP-2925.

* * * * *

UNITED STATES PATENT AND TRADEMARK OFFICE
CERTIFICATE OF CORRECTION

PATENT NO. : 5,272,067
DATED : DECEMBER 21, 1993
INVENTOR(S) : TAKAYASU TSUCHIDA ET AL

It is certified that error appears in the above-indentified patent and that said Letters Patent is hereby corrected as shown below:

Column 1, line 64, "FERM BP-2925" should read --FERM BP-2925)--.

Column 3, line 8, "machine. The pH of the culture" should read --machine.
The pH of the culture--.

Signed and Sealed this

Seventh Day of February, 1995

Attest:

BRUCE LEHMAN

Attesting Officer

Commissioner of Patents and Trademarks